United States Patent [19]

Williams

[11] Patent Number: 4,944,766
[45] Date of Patent: Jul. 31, 1990

[54] GRIPPING DEVICE

[76] Inventor: Brian R. Williams, 32802 Valle Rd. #32, San Juan Capistrano, Calif. 92675

[21] Appl. No.: 383,281

[22] Filed: Jul. 20, 1989

Related U.S. Application Data

[63] Continuation of Ser. No. 167,338, Mar. 14, 1988, abandoned.

[51] Int. Cl.$^5$ ............................................. A61F 2/68
[52] U.S. Cl. ........................................ 623/65; 401/6; 623/66
[58] Field of Search ............................. 623/65; 401/6

[56] References Cited

U.S. PATENT DOCUMENTS

| | | |
|---|---|---|
| 463,835 | 7/1910 | Twichell ................................ 401/6 |
| 1,318,260 | 10/1919 | Bosch . |
| 1,344,357 | 6/1920 | Shirer . |
| 1,378,578 | 5/1921 | Bauman . |
| 1,819,317 | 8/1931 | Baehr . |
| 1,989,960 | 2/1935 | Wheeler et al. . |
| 2,347,900 | 3/1943 | Jarrett . |
| 2,494,734 | 1/1950 | Wilkinson . |
| 2,566,215 | 8/1951 | La Croix . |
| 2,889,160 | 6/1959 | Nelson . |
| 3,020,908 | 2/1962 | Daniels ................................. 128/77 |
| 3,036,412 | 5/1962 | Larsen et al. . |
| 3,434,163 | 3/1969 | Saverino . |
| 3,942,194 | 3/1976 | Winter . |
| 4,357,717 | 11/1982 | Puhl . |
| 4,386,448 | 6/1983 | Kohn ..................................... 401/6 |
| 4,523,781 | 6/1985 | Brody . |
| 4,784,120 | 11/1988 | Thomas ................................ 128/77 |

OTHER PUBLICATIONS

Product Description of the Futuro Company of Cincinnati, Ohio, showing a Commercially available Wrist Brace (a FUTRO adjustable wrist brace).

Primary Examiner—Richard J. Apley
Assistant Examiner—James Prizant
Attorney, Agent, or Firm—Gordon L. Peterson; Loyal M. Hanson

[57] ABSTRACT

A prosthetic gripping device includes an elongated support member haivng first and second end portions and an intermediate portion extending between the first and second end portions, a gripping head attached to the second end portion for holding an implement, and a sleeve to be secured on the arm of a user in order to hold the first end portion of the support member on the arm. The first end portion of the support member is dimensioned and arranged to be held on the arm by the sleeve in a position adjacent the inner wrist such that the support member extends toward the hand, the intermediate portion is dimensioned and arranged to curve slightly over the heel of the hand, and the second end portion is dimensioned and arranged to extend to the palm of the hand with the gripping head being thereby supported at the palm of the hand. Angled slots and holes may be provided in the gripping head for advantageous implement position, and the support member and sleeve may be arranged as a wrist brace to provide wrist support.

22 Claims, 2 Drawing Sheets

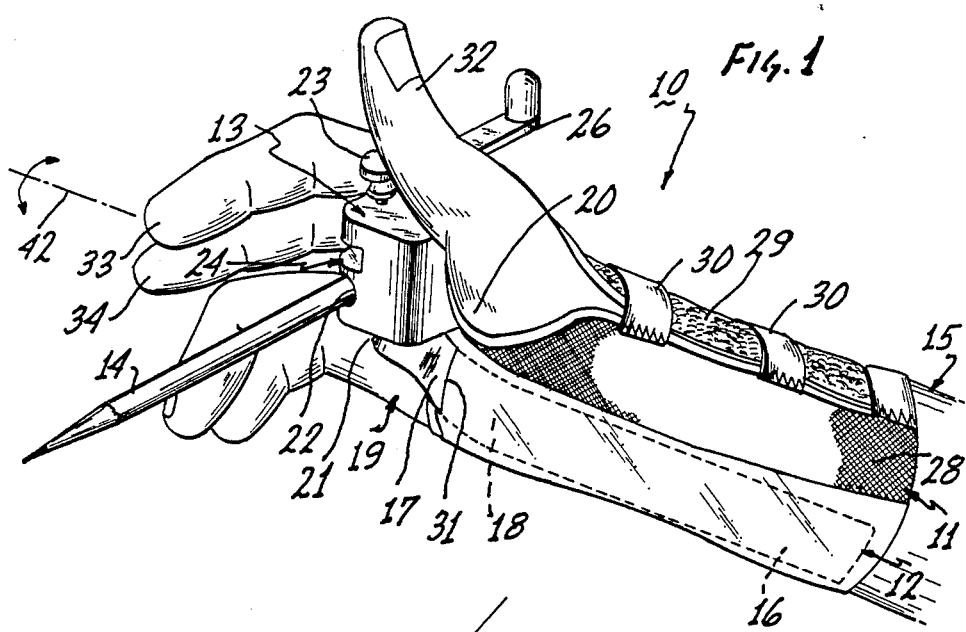
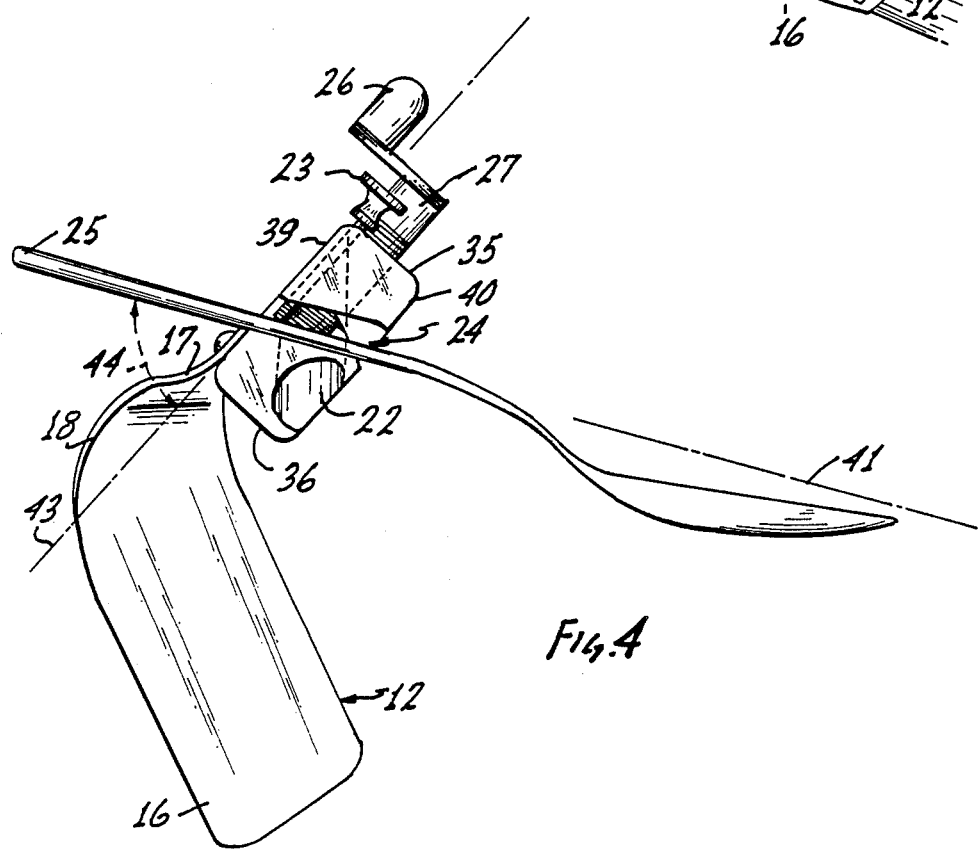

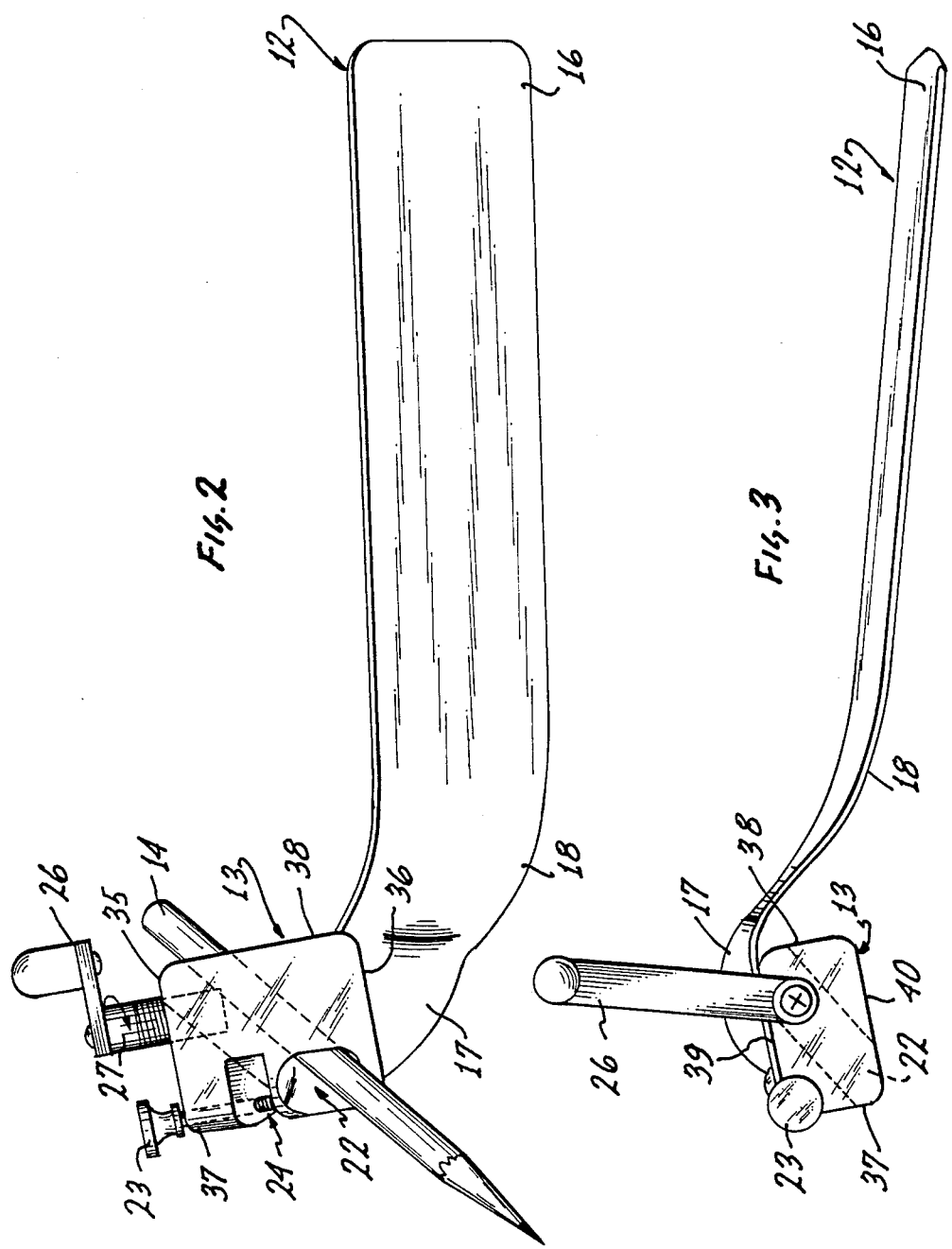

GRIPPING DEVICE

This application is a continuation of application Ser. No. 167,338, filed Mar. 14, 1988, and also entitled "Gripping Device," now abandoned.

BACKGROUND OF THE INVENTION

1. Technical Field

This invention relates generally to prosthetic devices, and more particularly to a gripping device that enables a physically impaired person to hold and use such common implements as eating and writing utensils.

2. Background Information

A quadriplegic condition, for example, may include virtual paralysis of the hand and a substantial reduction in arm movement. This greatly complicates performance of tasks requiring manipulation of an object. Thus, prosthetic devices that alleviate this concern are of particular interest.

However, existing devices for gripping objects have certain drawbacks that need to be overcome. They may be complicated and cumbersome. They may involve harnesses and hardware that are costly to fabricate and inconvenient to use. In addition, they may be somewhat unsightly and thus cause embarrassment.

Furthermore, some devices are not suited for such diverse tasks as gripping and using a pencil to write, gripping and using a object to punch the keys of a calculator, and gripping and using a fork or spoon in order to eat. Each of these tasks involve different arm movements that the device must accommodate.

Consequently, it is desirable to have a new and improved prosthetic or gripping device that alleviates these concerns.

SUMMARY OF THE INVENTION

This invention solves the problems outlined above by utilizing a wrist brace to support a gripping head at the palm of the hand. The wrist brace includes a sleeve that holds an elongated member or splint in a position such that the splint extends along the inner wrist, curves slightly over the heel of the hand, and extends to the gripping head at the palm. This arrangement provides wrist support while positioning the gripping head unobtrusively within the hand where various implements can be attached at advantageous angles, thereby relieving the user from unsightly harnesses and hardware and providing superior performance.

Generally, a prosthetic gripping device constructed according to the invention includes an elongated support member having first and second end portions and an intermediate portion extending between the first and second end portions, a gripping head attached to the second end portion for holding an implement, and a sleeve to be secured on the arm of a user in order to hold the first end portion of the support member on the arm.

The first end portion of the support member is dimensioned and arranged to be held on the arm by the sleeve in a position adjacent the inner wrist such that the support member extends toward the hand. The intermediate portion is dimensioned and arranged to curve slightly over the heel of the hand, and the second end portion is dimensioned and arranged to extend toward the palm of the hand with the gripping head being thereby supported at the palm of the hand.

According to another aspect of the invention, the sleeve and elongated member combine as a wrist brace to provide wrist support as well. According to yet another aspect of the invention, the gripping head is arranged to accommodate various implements and hold them at angles suited to their use.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 of the drawings is a perspective view of a gripping device constructed according to the invention;

FIG. 2 is an enlarged elevation view of the gripping device with a pencil mounted in the angled hole;

FIG. 3 is an enlarged plan view with the pencil removed; and

FIG. 4 is an enlarged end view with a spoon mounted in the angled slot.

DESCRIPTION OF THE PREFERRED EMBODIMENTS

Referring now to FIG. 1, there is shown a prosthetic gripping device 10 constructed according to the invention. It includes a sleeve 11, an elongated support member 12, and a gripping head 13 that combine to hold an implement, such as a writing implement or pencil 14 in the position shown on an arm 15. The gripping head 13 is also configured to hold other implements as subsequently described.

The support member 12 has a first end portion 16, a second end portion 17, and an intermediate portion 18 extending between the first and second end portions 16 and 17. The first end portion 16 is dimensioned and arranged to be held on the arm 15 by the sleeve 11 in a position adjacent the inner wrist of the arm 15 such that the splint 12 extends toward the hand 19. The sleeve 11 holds it in this position.

The intermediate portion 18 is dimensioned and arranged to curve slightly over the heel 20 of the hand 19, and the second end portion 17 is dimensioned and arranged to extend toward the palm 21 of the hand 19 with the gripping head 13 being thereby supported generally at the palm 21.

In this position, the gripping head 13 is somewhat concealed within the hand 19 where it is used as gripping means for holding the pencil 14. The gripping head 13 defines a passage 22 in which the pencil 14 is retained by operation of a crank 26 on a threaded shaft 27 (FIG. 1) and a slot 24 in which an eating implement such as a spoon 25 is retained by operation of a thumbscrew 23 (FIG. 4). The crank 26 is provided for a user capable of turning it, but two thumbscrews can be provided instead.

Of course, other implements may be held in the passage 22 and slot 24 and other means may be employed to secure them there. In this regard, the thumbscrew 23 and the threaded shaft 27 serve as means for securing an implement in respective ones of the slot 24 and the passage 22, and each combines with the respective one of the slot 24 and the passage 22 to serve as means for holding an implement. The threaded shaft 27 bears against the pencil 14 for this purpose, and the thumbscrew 23 bears against the spoon 25.

According to another aspect of the invention, various aspects of the sleeve 11 and support member 12 may be configured as a wrist brace according to the wrist brace description in U.S. Pat. No. 3,327,703. Doing this augments implement gripping components with significant wrist support that greatly facilitates implement operation by a physically impaired user, and that patent is incorporated by reference for the details of construction provided.

A commercially available wrist brace sleeve may also be employed, such as the wrist brace sold under the trademark FUTURO by the Jung Corporation of Cincinnati, Ohio. Like some commercially available wrist brace sleeves, the sleeve 11 employs an elastic member 28 that is secured by conventional loop-and-hook fastener having a loop component 29 that is engaged by hook components 30 (FIG. 1). A loop-and-hook fastener such as that sold under the trademark VELCRO by Velcro USA Inc. of Manchester, N.H. may be used for this purpose.

The sleeve 11 includes a pocket in which the elongated member 12 is retained as illustrated in FIG. 1, the pocket extending to a slit 31 in the sleeve 11 through which the support member 12 extends. Wrist brace models No. 33R and 33L of the Jung Corporation mentioned above (for right and left hand use respectively) include a pocket in which a splint member is retained, and the splint member may be removed and a slit such as the slit 31 formed in the wrist brace sleeve to adapt it for use according to the instant invention.

In this regard, the support member 12 may be have a size and shape somewhat similar to the wrist brace splint that is removed. However, various other kinds and types of sleeves and support members may be utilized within the broader inventive concepts disclosed.

The illustrated support member 12 is in the form of a generally flat blade about eighteen centimeters long and three to four centimeters wide. It addition, it is composed of a somewhat malleable aluminum alloy between one and two millimeters thick. This provides sufficient rigidity for wrist support purposes and purposes of supporting the gripping head 13, while enabling a slight amount of manual shaping of the support member 12 for purposes of fitting it to the user. Of course, these dimensions are not critical.

The intermediate portion 18 of the support member 12 curves over the heel 20 of the hand and toward the palm 21 as well as slightly toward the thumb 32 (FIG. 1). This positions the gripping head 13 toward the index finger 33. As a result, the pencil 14 is held in a conventional writing position. In other words, if the index finger 33 and the second finger 34 are moved toward the pencil 14 and the thumb 32 is moved opposite those fingers toward the pencil 14, the pencil 14 would be cradled between the thumb and fingers in a position extending generally parallel to the index finger 33 (FIG. 1).

Although other materials may be employed, the gripping head 13 is composed of an aluminum alloy. It is attached to the support member 12 by suitable means, such as machine screws that extend through holes in the support member 12 into the gripping head 13. As an idea of size, the gripping head 13 is approximately three and one-half centimeters high between opposite surfaces 35 and 36 (FIGS. 2 and 4), three centimeters wide between opposite surfaces 37 and 38 (FIGS. 2 and 3), and two centimeters thick between opposite surfaces 39 and 40 (FIGS. 3 and 4).

Of course, these dimensions are not critical and the size and shape may be changed to suit various users. Preferably, the gripping head 13 is large enough to hold implements while being small enough to remain somewhat concealed within the hand 19.

As mentioned above, the pencil 14 is held in a position approximating a conventional writing position. In this regard, the hole 22 is configured so that the gripping head 13 holds the pencil 14 inclined downwardly from the surface 35 approximately forty-five degrees and inclined forwardly from the surface 38 approximately sixty degrees. These angles may vary somewhat according to the precise alignment desired. In this regard, the pencil or other implement may be used within the passage 22 as a stylus for such things as operating a computer keyboard, for example.

The spoon 25 is advantageously aligned also. The slot 24 is configured so that the gripping head 13 holds the spoon 25 inclined upwardly from the surface 36. The spoon 25 extends along a line 41 (FIG. 4), and this line lies in a plane that is generally perpendicular to the axis 42 of the arm 15 (FIG. 1), more particular, the axis of a forearm portion of the arm 15.

The surface 39 lies in a plane 43 (FIG. 4) and this plane is generally the plane of the palm 21. The line 41 along which the spoon 25 extends is inclined to the plane 43 toward the thumb 32, intersecting the plane 43 at an angle 44 (FIG. 4) which is about fifteen to about thirty degrees, preferably approximately twenty-five degrees.

This arrangement greatly facilitates use of the spoon 25 or other eating implement. Rotating the arm 15 about the axis 42 (FIG. 1) to direct the spoon 25 downwardly, the user advances the spoon 25 toward the food, soup for example. After a quantity of soup flows into the spoon 25, the user bends the elbow joint to lift the hand 19 while rotating the arm 15 about the axis 42 to reposition the spoon 25 upwardly and advance the spoon 25 to the mouth.

With the spoon 25 held by the gripping head 13 at the angle described, this can be accomplish without lifting the elbow significantly. In other words, lifting the elbow or upper arm as required by some other gripping devices results in an involuntary internal rotation of the hand which may result in food falling off of the implement.

The conventional position for an eating implement is either inclined downwardly away from the palm and the thumb or positioned over the thumb (the palmer position). These positions result in the elbow having to be raised in order to scoop food onto and prevent food from falling off of the implement.

Inclining the eating implement in the manner of this invention alleviates this concern to greatly facilitate use of the spoon 25 or other eating implement. In addition, the sleeve 11 and support member 12 provide wrist support. Moreover, the gripping head 13 is positioned unobtrusively within the hand where various implements can be attached at advantageous angles, thereby relieving the user from unsightly harnesses and hardware and providing superior performance.

Although an exemplary embodiment of the invention has been shown and described, many changes, modifications, and substitutions may be made by one having ordinary skill in the art without necessarily departing from the spirit and scope of the invention.

What is claimed is:

1. A prosthetic device, comprising:

an elongated support member having first and second end portions and an intermediate portion extending between the first and second end portions; and gripping means attached to the second end portion of the elongated support member for holding first and second implements so that a user can support a selected one of the first and second implements in a hand of the user without having to grip the selected one;

the first end portion being dimensioned and arranged to be held on the arm of the user with the first end portion in a position adjacent the inner wrist such that the support member extends toward the hand;

the intermediate portion being dimensioned and arranged to curve slightly over the heel of the hand;

the second end portion being dimensioned and arranged to extend toward the palm of the hand with the gripping means supported generally at the palm of the hand; and the gripping means being configured so that the first implement is held in a position approximating a conventional writing position and so that the second implement is held in a position such that the second implement extends along a line that lies in a plane generally perpendicular to the axis of the arm, which line is inclined to the plane of the palm toward the thumb.

2. A device as recited in claim 1, wherein the gripping means includes:
a gripping head attached to the second end portion, the gripping head including means for holding a writing implement.

3. A device as recited in claim 2, wherein the means for holding a writing implement includes:
a passage extending within the gripping head, which hole is dimensioned and arranged to receive the writing implement; and
means for securing the writing implement within the passage.

4. A device as recited in claim 3, wherein the means for securing the writing implement includes:
a thumbscrew extending within the gripping head to the passage that operates to bear against the writing implement and thereby secure it within the passage.

5. A device as recited in claim 3, wherein the means for securing the writing implement includes:
a threaded shaft extending within the gripping head to the passage that operates to bear against the writing implement; and
a crank member operatively attached to the threaded shaft.

6. A device as recited in claim 3, wherein:
the passage is arranged to hold the writing implement in a conventional writing position relative to the hand.

7. A device as recited in claim 1, wherein the gripping means includes:
a gripping head attached to the second end portion, the gripping head including means for holding an eating implement.

8. A device as recited in claim 7, wherein the means for holding an eating implement includes:
a slot extending within the gripping head, which slot is dimensioned and arranged to receive the eating implement; and
means for securing the eating implement within the slot.

9. A device as recited in claim 8, wherein the means for securing the eating implement includes:
a thumbscrew extending within the gripping head to the slot that operates to bear against the eating implement and thereby secure it within the slot.

10. A device as recited in claim 8, wherein:
the slot is arranged to hold the eating implement in a position such that the eating implement extends along a line that lies in a plane generally perpendicular to the axis of the arm, which line is inclined to the plane of the palm toward the thumb.

11. A device as recited in claim 10, wherein:
the line is inclined to the plane of the palm from about fifteen to about thirty degrees.

12. A device as recited in claim 10, wherein:
the line is inclined to the plane of the palm approximately twenty-five degrees.

13. A device as recited in claim 1, wherein the support member includes:
a generally flat blade composed of a material that is sufficient rigid to enable the support member to support the gripping means and sufficient malleable to enable manual shaping for purposes of adjusting the support member to a particular user.

14. A device as recited in claim 1 further comprising:
a sleeve in the form of an elastic body having loop-and-hook fastener means for attaching the elastic body around the arm in a position disposed generally over the wrist.

15. A device as recited in claim 14, wherein the sleeve includes:
a pocket in the sleeve arranged to extend along the wrist and receive the support member in order to hold the support member adjacent the wrist.

16. A prosthetic device, comprising:
a wrist brace having a sleeve and an elongated support member, which sleeve is arranged to be secured on the arm of a user in order to hold the support member adjacent the inner wrist for wrist support purposes; and gripping means attached to the support member for holding first and second implements so that a user can support a selected one of the first and second implements in a hand of the user without having to grip the selected one;

the support member having first and second end portions and an intermediate portion extending between the first and second end portions;

the first end portion being dimensioned and arranged to be held on the arm by the sleeve in a position adjacent the inner wrist such that the support member extends toward the hand;

the intermediate portion being dimensioned and arranged to curve slightly over the heel of the hand;

the second end portion being dimensioned and arranged to extend toward the palm of the hand with the gripping means being thereby supported generally at the palm of the hand; and the gripping means being configured so that the first implement is held in a position approximating a conventional writing position and so that the second implement is held in a position such that the second implement extends along a line that lies in a plane generally perpendicular to the axis of the arm, which line is inclined to the plane of the palm toward the thumb.

17. A prosthetic device, comprising:

a generally flat blade having first and second end portions and an intermediate portion extending between the first and second end portions; and a gripping head attached to the second end portion of the elongated support member for holding first and second implements so that a user can support a selected one of the first and second implements in a hand of the user without having to grip the selected one; the first end portion being dimensioned and arranged to be held on the arm of the user by separate securing means secured on the arm of the user, with the first end portion in a position adjacent the inner wrist such that the blade extends toward the hand;

the intermediate portion being dimensioned and arranged to curve slightly over the heel of the hand;

the second end portion being dimensioned and arranged to extend toward the palm of the hand with the gripping head being thereby supported generally at the palm of the hand; and the gripping head being configured so that the first implement is held in a position approximating a conventional writing position and so that the second implement is held in a position such that the second implement extends along a line that lies in a plane generally perpendicular to the axis of the arm, which line is inclined to the plane of the palm toward the thumb.

18. A device as recited in claim 17, wherein the gripping head includes:

a body of material dimensioned and arranged to enable placement in the hand of the user, the body of material defining first and second passages in which to receive respective ones of a writing implement and an eating implement, the first and second passages extending along respective ones of first and second axes that extend generally transversely to each other in order to adapt the gripping head for both writing and eating.

19. A device as recited in claim 18, wherein:

the second passage opens sidewardly to facilitate fabrication and the insertion of an eating implement.

20. A prosthetic device, comprising:

an elongated support member having first and second end portions; and gripping means attached to the elongated support member adjacent the second end portion for holding first and second implements in a generally transverse relationship to each other so that a user can support a selected one of the first and second implements in a hand of the user without having to grip the selected one;

the elongated support member being dimensioned and arranged to be held on the arm of the user with the first end portion adjacent the inner wrist and with the gripping means being supported generally at the palm of the hand.

21. A prosthetic device as defined in claim 20 wherein the gripping means includes a block having at least one opening sized to receive an implement and means for affixing the implement in the opening, and the prosthetic device includes means for mounting the block on the support member adjacent the second end of the blade whereby the block is in the hand of the user.

22. A prosthetic device as defined in claim 20 wherein the first end portion is generally flat and the support member has a curved intermediate portion.

* * * * *